United States Patent
Tanaka et al.

(10) Patent No.: US 6,974,963 B2
(45) Date of Patent: Dec. 13, 2005

(54) SUBSTRATE INSPECTING DEVICE, COATING/DEVELOPING DEVICE AND SUBSTRATE INSPECTING METHOD

(75) Inventors: Michio Tanaka, Kumamoto (JP);
Makoto Kiyota, Kumamoto (JP);
Takashi Aiuchi, Kumamoto (JP);
Ryouichi Uemura, Kumamoto (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/494,524

(22) PCT Filed: Nov. 13, 2002

(86) PCT No.: PCT/JP02/11835

§ 371 (c)(1),
(2), (4) Date: Oct. 1, 2004

(87) PCT Pub. No.: WO03/043064

PCT Pub. Date: May 22, 2003

(65) Prior Publication Data

US 2005/0038618 A1 Feb. 17, 2005

(30) Foreign Application Priority Data

Nov. 14, 2001 (JP) .................................. 2001-348742

(51) Int. Cl.$^7$ .............................................. G01N 21/86
(52) U.S. Cl. .................. 250/548; 250/559.39; 356/394; 356/237.2
(58) Field of Search ........................... 250/548, 559.02, 250/559.2, 559.29, 559.3, 559.39; 356/399–401, 388, 394, 635, 636, 237.2, 237.5; 430/30

(56) References Cited

U.S. PATENT DOCUMENTS 5,361,137 A * 11/1994 Aton et al. ................. 356/496

FOREIGN PATENT DOCUMENTS

| JP | 63-237521 | 10/1988 |
|----|-----------|---------|
| JP | 5-136025 | 6/1993 |
| JP | 7-22307 | 1/1995 |
| JP | 11-340115 | 12/1999 |
| JP | 2002-15980 | 1/2002 |
| WO | 00/57126 | 9/2000 |

* cited by examiner

*Primary Examiner*—Kevin Pyo
(74) *Attorney, Agent, or Firm*—Oblon, Spivak, McClelland, Maier & Neustadt, P.C.

(57) ABSTRACT

When a base film of a substrate is formed, for instance, on a scribe line of a wafer, a quadrangular first inspection pattern is formed in advance, and when a resist pattern is formed, a second inspection pattern are formed so as to be on a straight line to the first inspection pattern in a top plan view. When light is irradiated to a region including the first inspection pattern and the second inspection pattern and a spectrum is formed based on the reflected diffracted light, information of a line width of the second inspection pattern and a pitch of both inspection patterns is contained therein. In this connection, by preparing in advance a group of spectra based on various kinds of inspection patterns according to simulation and by comparing with an actual spectrum, the most approximate spectrum is selected, and thereby the line width and the pitch are estimated to evaluate the resist pattern.

12 Claims, 16 Drawing Sheets

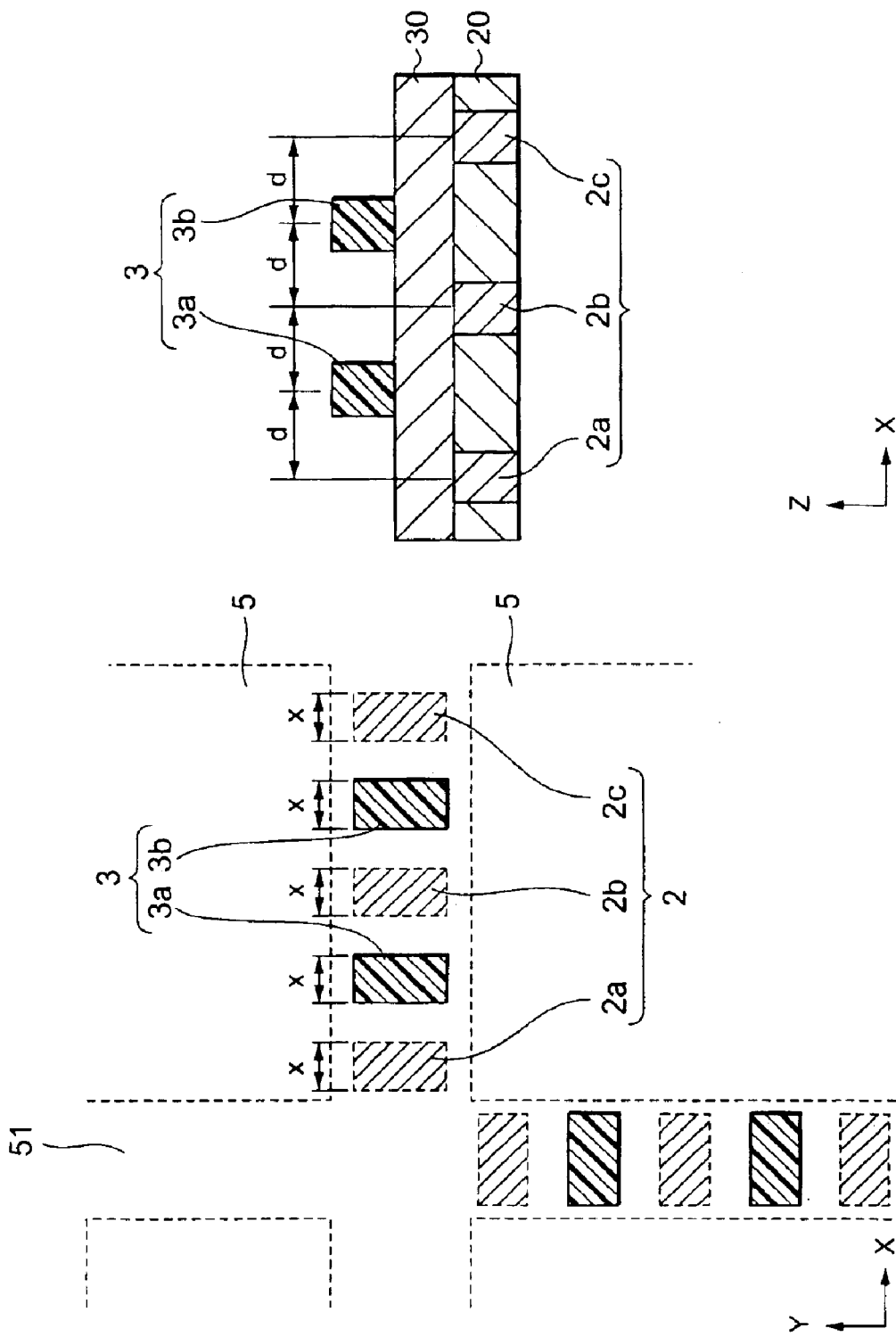

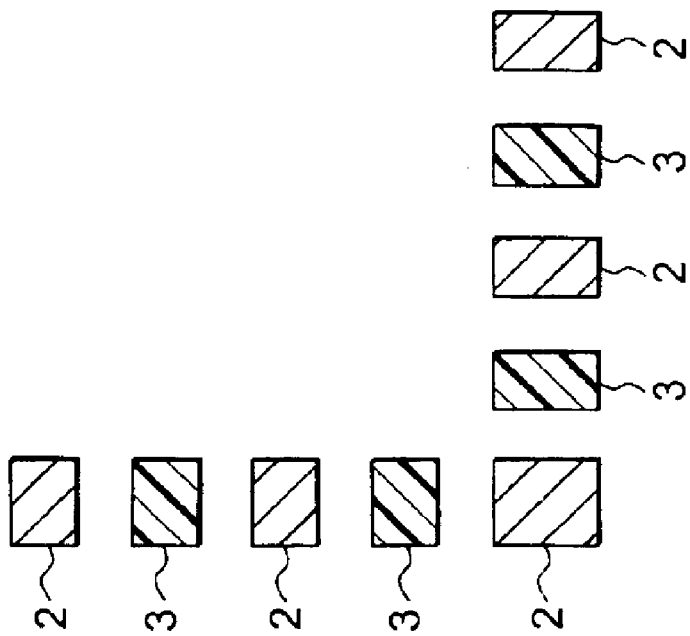
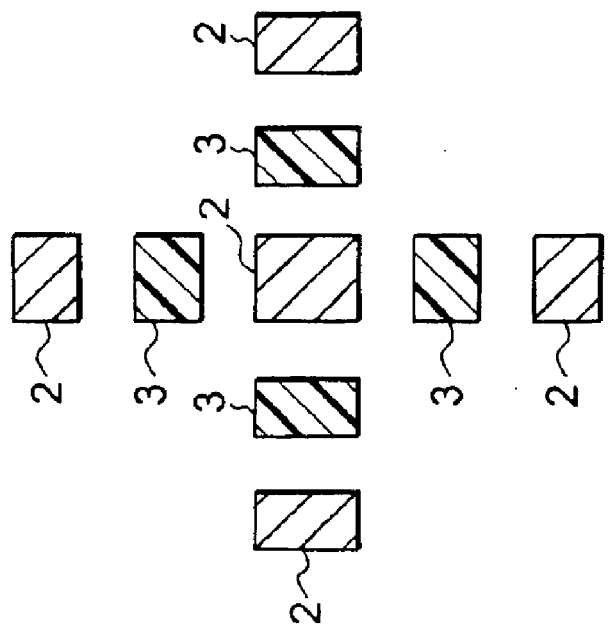

SUBSTRATE INSPECTING DEVICE, COATING/DEVELOPING DEVICE AND SUBSTRATE INSPECTING METHOD

TECHNICAL FIELD

The present invention relates to a substrate inspection apparatus for inspecting a resist pattern formed on, for instance, a substrate, a coating/developing apparatus provided with the inspection apparatus and a substrate inspection method.

BACKGROUND ART

So far, in a photo-resist process, one of semiconductor manufacturing processes, for instance, a resist is coated on a surface of a semiconductor wafer (hereinafter referred to as an wafer W), the resist is exposed with a predetermined pattern followed by developing, and thereby a resist pattern is formed. Such process is generally carried out using a system in which an aligner is connected to a coating/developing apparatus that coats and develops the resist.

In the substrate processing, it is necessary that a line width of the resist pattern is formed with a predetermined line width and resist patterns in X and Y directions of the resist pattern is formed as scheduled relative to a pattern already formed on a base film at a surface portion (i.e. a thin film to be etched with the resist pattern) on which the resist pattern is formed. For this reason, conventionally a line width and positional relationship (overlay) in a horizontal direction with respect to the base film is inspected by use of, for instance, a stand-alone type inspection apparatus disposed separately from a coating/developing apparatus. The inspection of the line width has been carried out by bombarding an electron beam on a surface of a substrate using an inspection unit with a scanning electron microscope (SEM), followed by analyzing a reflection output thereof. Furthermore, as to the overlay, large and small patterns for inspection 1, with each of them being a quadrangular type (1a and 1b) is formed on the base film by using an inspection unit provided with an optical system with a diffraction grating, and the light is irradiated with a light source scanning and reflection intensity is analyzed, thereby, as shown in FIG. 17B, whether a projection of a small inspection pattern 1a falls within a large inspection patter 1b or not is investigated, and thereby the overlay has been inspected.

However, according to the above-mentioned method, various problems remain to be solved as explained below. In other words, depending on inspection items, a plurality of inspection units is used for processing; as a result, including a length of time for transferring the substrate between the respective units, a length of time necessary for inspection is also quite long, resulting in being one of the causes of the deterioration of throughput, and a footprint of the inspection apparatuses is large. Furthermore, when a defect of the resist pattern occurs for the subsequent substrates, similar defect pattern is likely to occur different in demand to inspect as speedily as possible.

DISCLOSURE OF THE INVENTION

The present invention is achieved under these circumstances and intends to provide a technology that can shorten a time necessary for inspection and make a foot print of an inspection apparatus smaller.

A substrate inspection apparatus for inspecting a substrate with a resist being coated on a surface thereof and the coated resist being performed with exposing and developing process, comprising:

a substrate mounting portion for mounting the substrate,
light irradiating means for irradiating a light having a predetermined wavelength from a surface side of the substrate to a region including a first inspection pattern formed on a base film and a second inspection pattern formed on a resist,
a light detection portion for detecting the light irradiated from the light irradiating means and reflected at the surface of the substrate,
means for preparing a spectrum for an inspection pattern from a diffracted light based on an output detected by the light detection portion,
means for preparing, by variously varying the respective line widths of the first inspection pattern and the second inspection pattern and mutual positional relationships in a horizontal direction of the first inspection pattern and the second inspection pattern, the group of spectra for comparison respectively corresponding to combinations of the line width of the second inspection pattern and the mutual positional relationship; and
comparison and selection means for comparing the group of spectra for comparison and the spectrum for inspection pattern and selecting one most approximate to the spectrum for inspection among the group of spectra for comparison;
wherein from the selected spectrum for comparison, a line width of the second inspection pattern which is a resist pattern formed on the substrate, and the positional relationship in a horizontal direction on the substrate are estimated.

The present invention is more specifically constituted, for instance, as follows. A judgment means for judging whether the line width of the resist pattern and the mutual positional relationship in a horizontal direction of the resist pattern and the base film are proper or not on the basis of the line width and the positional relationship of the second inspection pattern corresponding to the selected spectrum for comparison and an allowable line width and allowable positional relationship of the second inspection pattern. Each of the first inspection pattern and the second inspection pattern is formed into, for instance, a quadrangle and arranged alternately on a straight line in a top plan view of the substrate. Alternately, each of the first inspection pattern and the second inspection pattern is formed into, for instance, a quadrangle and arranged on the same position on a straight line in a top plan view of the substrate. As the inspection pattern, a set in which these inspection patterns are arranged on a straight line in an X direction and a set in which the first inspection pattern and the second inspection pattern are arranged in a Y direction on a straight line are prepared, for each of the sets a spectrum for inspection pattern is formed and for each of spectra for inspection of the respective sets a most approximate spectrum for comparison is selected, and whether mutual positional relationship in a X direction of the resist pattern and base film and mutual positional relationship in a Y direction each are appropriate or not maybe judged based on the spectra for comparison.

The first inspection pattern and the second inspection pattern are arranged, for instance, equally spaced, and formed, for instance, on a scribe line that is outside of an effective region of the substrate and cut for each chip. In addition, the means for preparing a group of spectra for comparison may be provided with simulation means for preparing a spectrum for comparison due to simulation based on the set of the line width and positional relationship.

Furthermore, as another configuration, a coating/developing apparatus including a mounting portion for mounting a substrate cassette housing a plurality of substrates, a coating unit for coating a resist on the substrate, a developing unit for developing an exposed substrate, a thermal unit for heating and cooling the substrate before or after the coating the resist on the substrate, or, before or after developing the substrate and transferring means for transferring a substrate between the mounting portion, the coating unit, the developing unit and the thermal unit may be provided with the substrate inspection apparatus described as above.

According to the substrate inspection apparatus according to the invention, in a single inspection apparatus, light having a predetermined wavelength is irradiated on the inspection pattern, a spectrum for inspection pattern obtained by detecting reflection light thereof and a group of spectra for comparison corresponding to various shapes of patterns are compared to select. Thereby, in a single inspection step, the line width of the resist pattern and an overlapping extent thereof with the base film can be simultaneously inspected. Accordingly, a time consumed for inspection can be shortened and a footprint of the inspection apparatus can be made smaller.

A substrate inspection method for inspecting a substrate with a resist being coated on a surface thereof and the coated resist being performed with exposing and developing process, comprising, transferring a substrate into a substrate mounting portion for mounting the substrate, irradiating a light having a predetermined wavelength from a surface side of the substrate to a region including a first inspection pattern formed on a base film and a second inspection pattern formed on a resist and detecting the light irradiated from the light irradiating means and reflected at the surface of the substrate with a light detection portion, preparing a spectrum for an inspection pattern from a diffracted light based on an output detected by the light detection portion, selecting one most approximate to the spectrum for inspection by comparing the spectrum for inspection pattern with a group of spectra which is prepared in advance by variously varying the respective line widths of the first inspection pattern and the second inspection pattern and mutual positional relationships in a horizontal direction of the first inspection pattern and the second inspection pattern, the group of spectra for comparison respectively corresponding to combinations of the line width of the second inspection pattern and the mutual positional relationship; and estimating a line width of the second inspection pattern which is a resist pattern formed on the substrate, and the positional relationship in a horizontal direction on the substrate.

Furthermore, a step of judging whether a line width of the resist pattern and a mutual positional relationship in a horizontal direction of the resist pattern and the base film are appropriate or not based on a line width and the positional relationship of the second inspection pattern corresponding to a selected spectrum for comparison and an allowable line width and an allowable positional relationship of the second inspection pattern may be added.

BRIEF DESCRIPTION OF DRAWINGS

FIGS. 4A and 4B are explanatory diagrams showing an inspection method of an inspection apparatus involving the present invention.

FIGS. 12A and 12B are explanatory diagrams showing another embodiment of the present invention.

BEST MODE OF CARRYING OUT THE INVENTION

Figure 1:
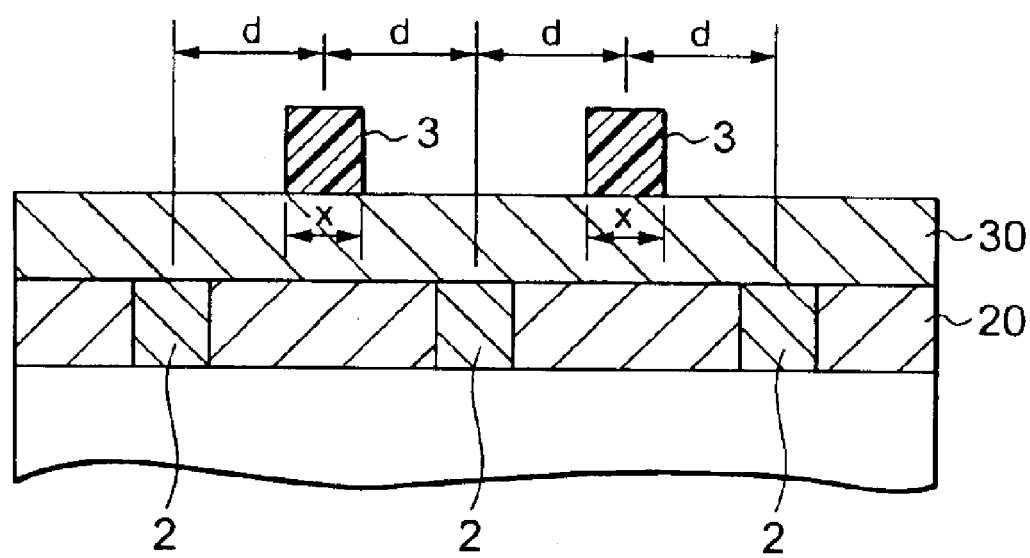
FIG. 1 is an explanatory diagram showing an inspection method of an inspection apparatus involving the present invention.
Figure 2A:
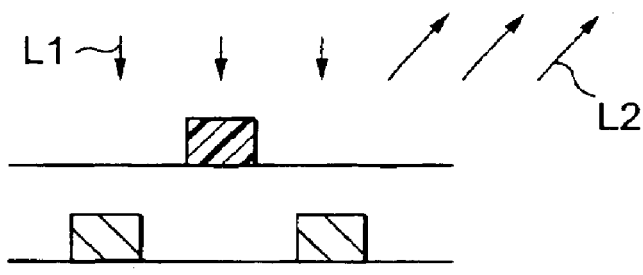
FIGS. 2A, 2B, 2C, 2D and 2E are explanatory diagrams showing an inspection method of an inspection apparatus involving the present invention.
Figure 2B:
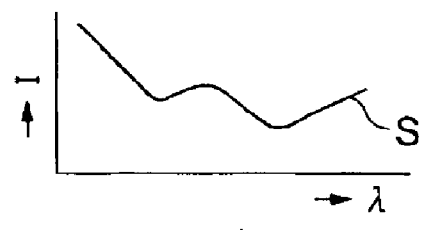

In explaining an embodiment according to the invention, a principle of inspection will be explained with reference to FIG. 1 and FIGS. 2A, 2B, 2C, 2D and 2E. An inspection is carried out to an inspection pattern constituted of a first inspection pattern 2 which is formed, as shown in FIG. 1, in a base film 20 formed on a substrate to be inspected and a second inspection pattern 3 which is a resist pattern formed on a surface of a film 30 at a surface portion, and a line width X of the second inspection pattern 3 and mutual positional relationship (pitch: d) in a horizontal direction of both inspection patterns (2,3) are items to be inspected. At the inspection, firstly, as shown in FIG. 2A, monochromatic light L1 having a particular wavelength is irradiated and diffracted light L2 of reflected light is detected, and thereby, as shown in FIG. 2B, a spectrum S for inspection pattern that shows relationship between wavelength $\lambda$ and light intensity I is obtained.

Figure 2C:
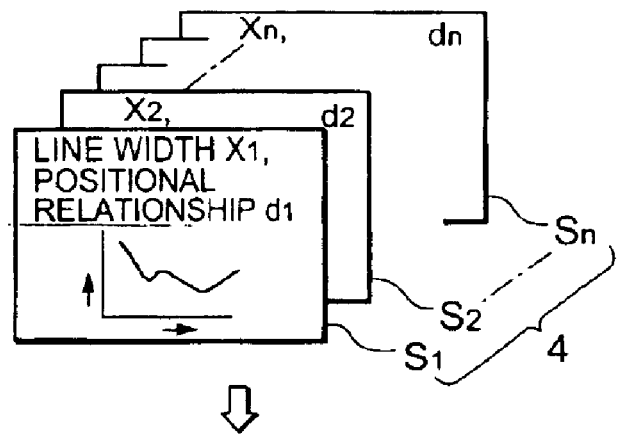
Figure 2D:
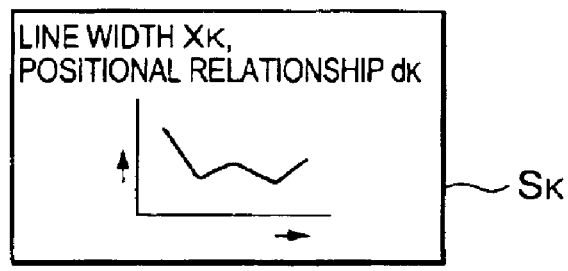

The inspection method according to the present invention pays attention to that in the spectrum S, information of the line width x and a mutual separation distance between a sidewall surface of the first inspection pattern and a sidewall surface of the second inspection pattern (a distance between the sidewall surface and an opposite sidewall surface in a top plan view) in a horizontal direction is contained. In this case, from the line width of the second inspection pattern and the separation distance, a pitch d that is mutual positional relationship in a horizontal direction between centerlines of both inspection patterns (2, 3) can be obtained, resultantly, the pitch d is also contained in the spectrum S as information. However, a pattern shape is not directly specified from the spectrum S. Instead, as shown in FIG. 2C, a data base 4 of a group of a plurality of spectra for comparison S1~Sn corresponding to pattern shapes in which various kinds of line widths x1, x2, ... xn and positional relationship (pitch) d1, d2, ... dn in a horizontal direction are combined is prepared in advance according to simulation. Then the spectrum S for inspection pattern and a group of spectra for comparison S1~Sn are compared, and, as shown in FIG. 2D, a spectra Sk the same as or most approximate to the spectrum S corresponding to the inspection pattern is selected from the group of spectra S1~Sn.

Figure 2E:
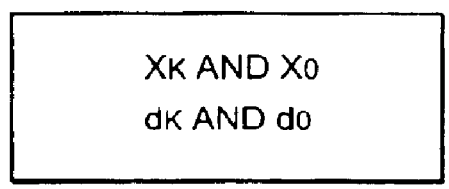

Subsequently, since a line width xk and a pitch dk corresponding to the spectrum for comparison selected from the group of spectra S1~Sn are known, as shown in FIG. 2E, the line width xk and the pitch dk are estimated to be the line width x (=xk) and the pitch d (=dk) of the both inspection patterns 2 and 3. Then, a line width accuracy can be obtained from a difference of the line width xk and a line width x0 (the ideal data) of a predetermined inspection pattern 3, and the positional (overlay) accuracy in a horizontal direction with respect to the base film can be obtained from a difference between the pitch dk and a predetermined pitch d0 (the ideal data).

Figure 3:
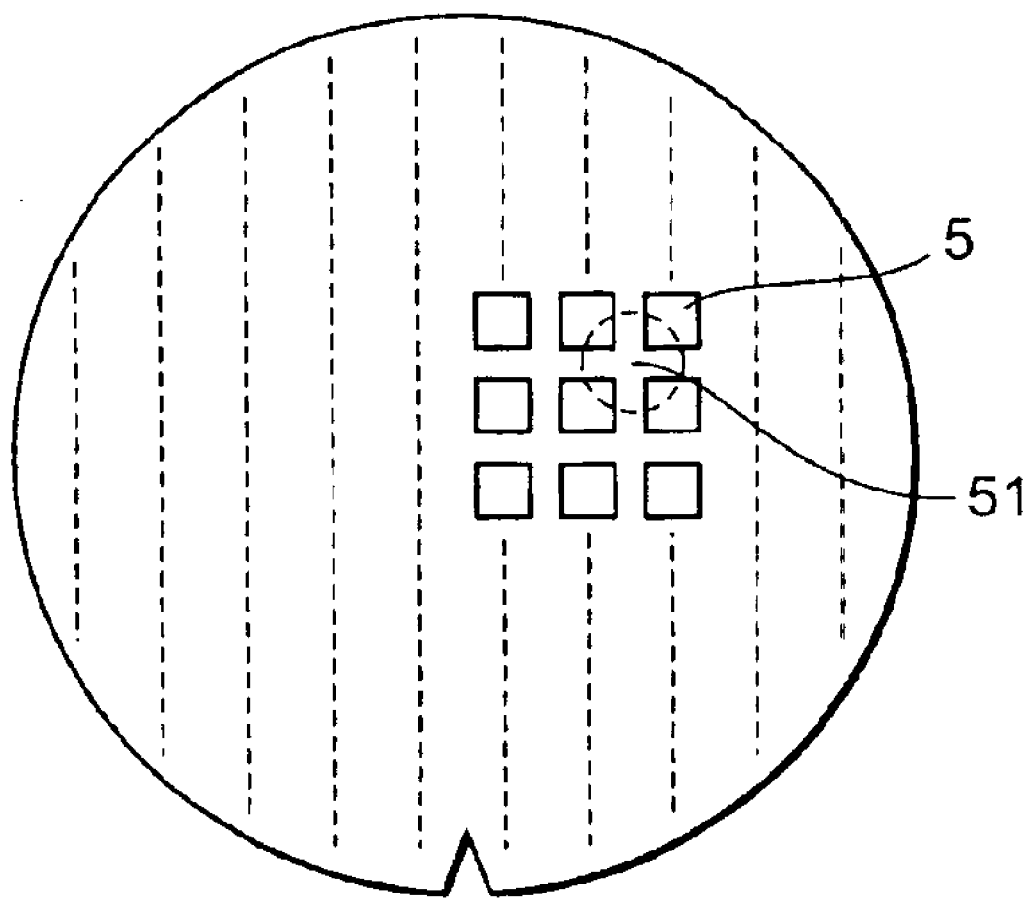
FIG. 3 is an explanatory diagram showing an inspection method of an inspection apparatus involving the present invention.

An inspection method of a substrate will be explained further in detail with reference to FIGS. 3, 4, 5 and 6. Firstly, the inspection patterns 2 and the inspection pattern 3 to be inspected are formed on a surface of a substrate to be inspected such as a semiconductor wafer (hereinafter, referred to as a wafer W) as shown in FIG. 3, and further in a region outside of a chip formation of an effective region 5 and finally becomes unnecessary such as a region of a scribe line 51 (i.e. a region between chips arranged horizontally and vertically and cut away with a diamond cutter and the like).

The inspection patterns are formed, for instance, as follows. As shown in FIG. 4, a detailed drawing of a dotted line portion of FIG. 3, a first inspection pattern 2 (2a, 2b and 2c) is formed in advance in a base film 20 of a wafer W. Then the wafer W on a film 30 of a surface portion of which a resist is coated is exposed with an exposure mask including a pattern corresponding to a second inspection pattern 3 (3a and 3b) followed by developing, and thereby the second inspection pattern 3 is formed. These inspection patterns (2 and 3) are formed so that a rectangular pattern having, for instance, length and breadth of 2 μm×5 μm in a planar shape may be alternately disposed on the base film and the resist in a straight line with a pitch d of, for instance, 5 μm separated equally in a top plan view. Here, a line width x of the second inspection pattern 3 that is an inspection target is a line width x in a direction of arrangement of the pattern (X direction). Furthermore, in order to investigate overlays in X-direction and Y-direction, two sets of patterns one of which is arranged in the X-direction and the other one is arranged in the Y-direction are preferably formed.

Figure 5A:
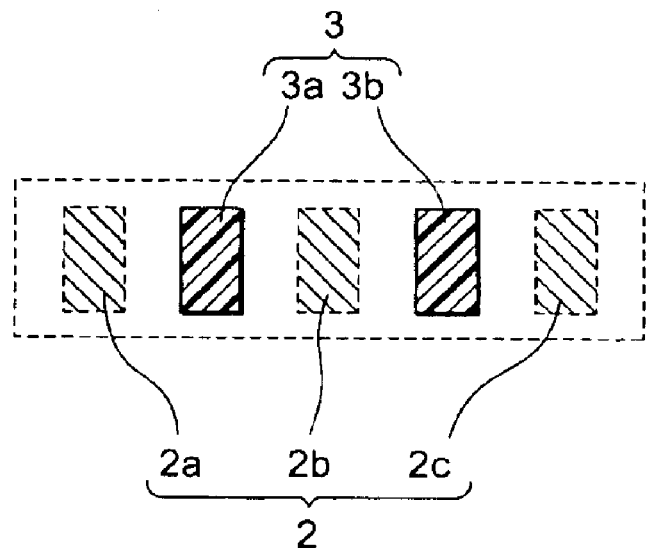
FIGS. 5A and 5B are explanatory diagrams showing an inspection method of an inspection apparatus involving the present invention.
Figure 5B:
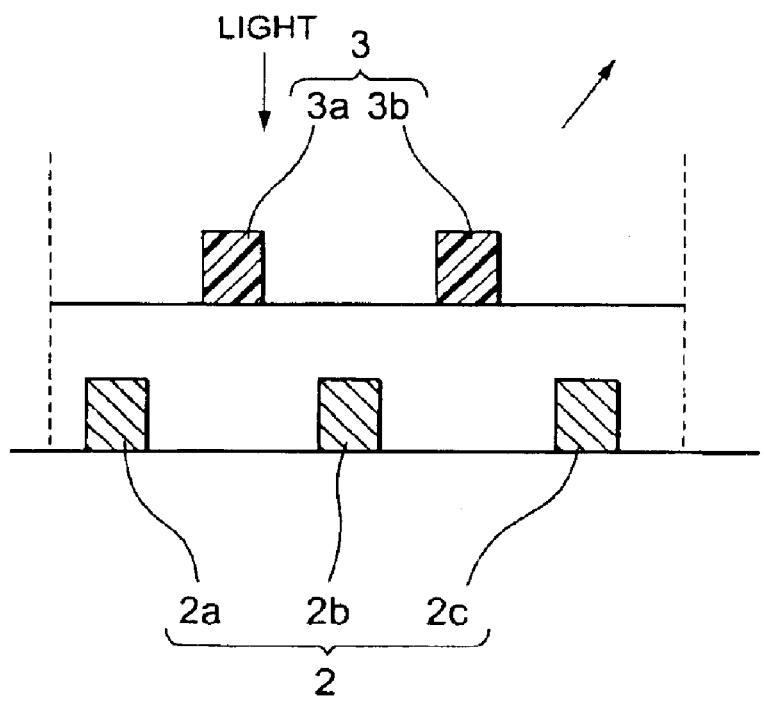
Figure 6:
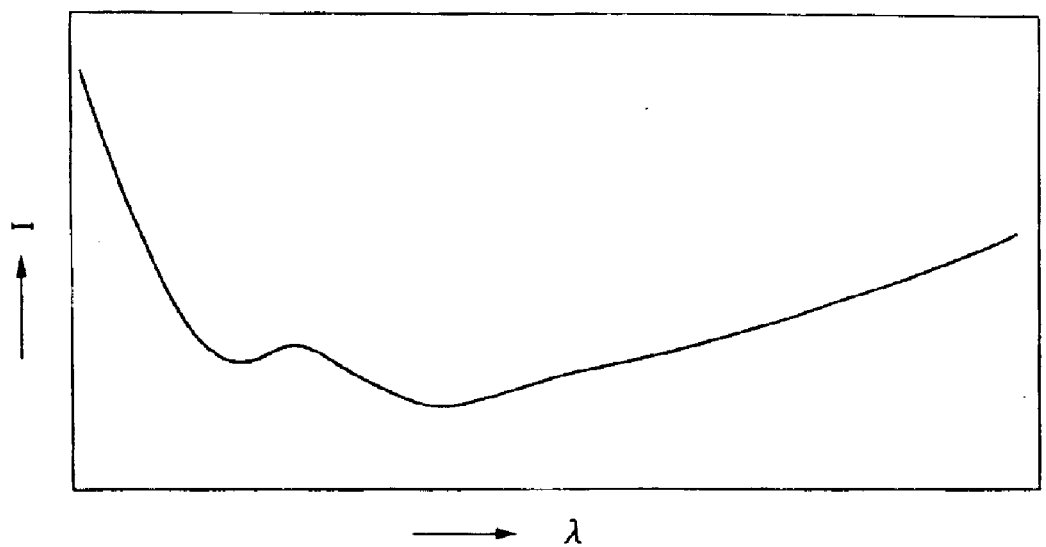
FIG. 6 is an explanatory diagram showing an inspection method of an inspection apparatus involving the present invention.

Subsequently, as schematically shown in FIG. 5A, monochromatic light such as light having a particular wavelength monochromatized from, for instance, a helium-neon laser having an irradiation region of a magnitude that can cover the region where the first inspection pattern 2 and the second inspection pattern 3 are arranged (i.e. dotted line portion in the drawing) is irradiated in a reflection manner as shown in, for instance, FIG. 5B. A diffracted light, which is a reflected light of the monochromatic light is detected, and thereby a spectrum S for inspection pattern indicating a relationship between wavelength λ and light intensity I and can be obtained as shown in FIG. 6. The spectrum S for inspection pattern exhibits waveforms corresponding to shapes of the inspection patterns such as waveforms respectively corresponding to the line width x and the pitch d. That is, when, for instance, a line width x of the inspection pattern varies, a waveform corresponding to the line width x also varies correspondingly, and when a pitch d varies, a waveform corresponding to the pitch d also varies correspondingly.

On the other hand, a group of spectra for comparison S1~Sn to be compared with the spectrum S for inspection pattern is assumed, and simulation is performed with a computer system so as to prepare a data base 4 of the group of spectra S1~Sn. Firstly, in order to assume a spectrum for comparison, a virtual model is formed. The virtual model is formed by arranging not only a line width x and a pitch d of a pattern to be inspected, but also values of parameters (specific values) such as a film thickness of the resist, a film quality of the resist, a film thickness of a base film and a film quality of the base film. In this case, in order to form the virtual model more specifically, the line width x of the pattern is preferably constituted so that, as shown in, for instance, FIG. 7, a line width $x_T$ at a top portion of the pattern, a line width $x_M$ at a middle portion of the pattern and a line width $x_B$ at a bottom portion of the pattern may be formed too.

Subsequently, to the pattern of the arranged virtual model, a waveform of a spectrum that would be obtained when monochromatic light is actually inputted is assumed according to the simulation. The simulation is carried out according to, for instance, the following method, however, a spectrum obtained beforehand by experiment by irradiating a pattern to obtain an actual shape thereof may be used and correction may be applied thereto. In the case of light being input in reflection manner as mentioned above, relationship between the wavelength λ and the light intensity I is detected. There, when the relationship between the wavelength λ and the light intensity I is derived by use of, for instance, a dispersion formula, a waveform of the spectrum can be assumed, and thereby a spectrum S1 is obtained. Furthermore, among parameters of the virtual model, the pitch d and the line width x (the line width xT at a top step of the pattern, line width xM at a middle step of the pattern and line width xB at a bottom step of the pattern), respectively, are varied in accordance with the inspection pattern in the range of 10 to 500 nm, for instance at separations of 130 nm and 150 nm, a group of spectra for comparison S2, S3, ... Sn corresponding to various kinds of combinations of these is also formed using similar means, and thereby a number of groups of spectra for comparison S2~Sn are obtained.

In the next place, waveforms of the spectrum S for inspection pattern and the group of spectra for comparison S1~Sn are compared and waveforms of both spectra are fitted by use of a mathematical method such as the partial least-square method, the multivariable analysis algorism and the minimum mean square error analysis. As a result, from the group of spectra for comparison S1~Sn, a spectrum Sk the same as or most approximate to the spectrum S for inspection pattern is selected. In this connection, the fitting may be applied to a waveform over an entire spectrum or to a portion corresponding to the line width x and the pitch d.

The selected spectrum for comparison $S_k$ is already known of the line width $x_K$ and the pitch $d_K$, therefore, the line width x and the pitch d of the spectrum for inspection pattern are estimated to be these line width $x_K$ and the pitch $d_K$. In other words, from results of the line width $x_K$ and the pitch $d_K$ of the resist pattern i.e. the second inspection pattern, the positional relationship (overlay) of the resist pattern and the base film in a horizontal direction can be estimated. Furthermore, from differences (deviation) from a scheduled line width x0 and a scheduled pitch d0 (ideal values), line width accuracy and overlay accuracy of the resist pattern can be obtained. As a result, the line width accuracy and overlay accuracy over the whole wafer W can be grasped, and whether the accuracies are acceptable or not is determined by checking whether these values are within the range of a previously-determined standard.

Figure 8:
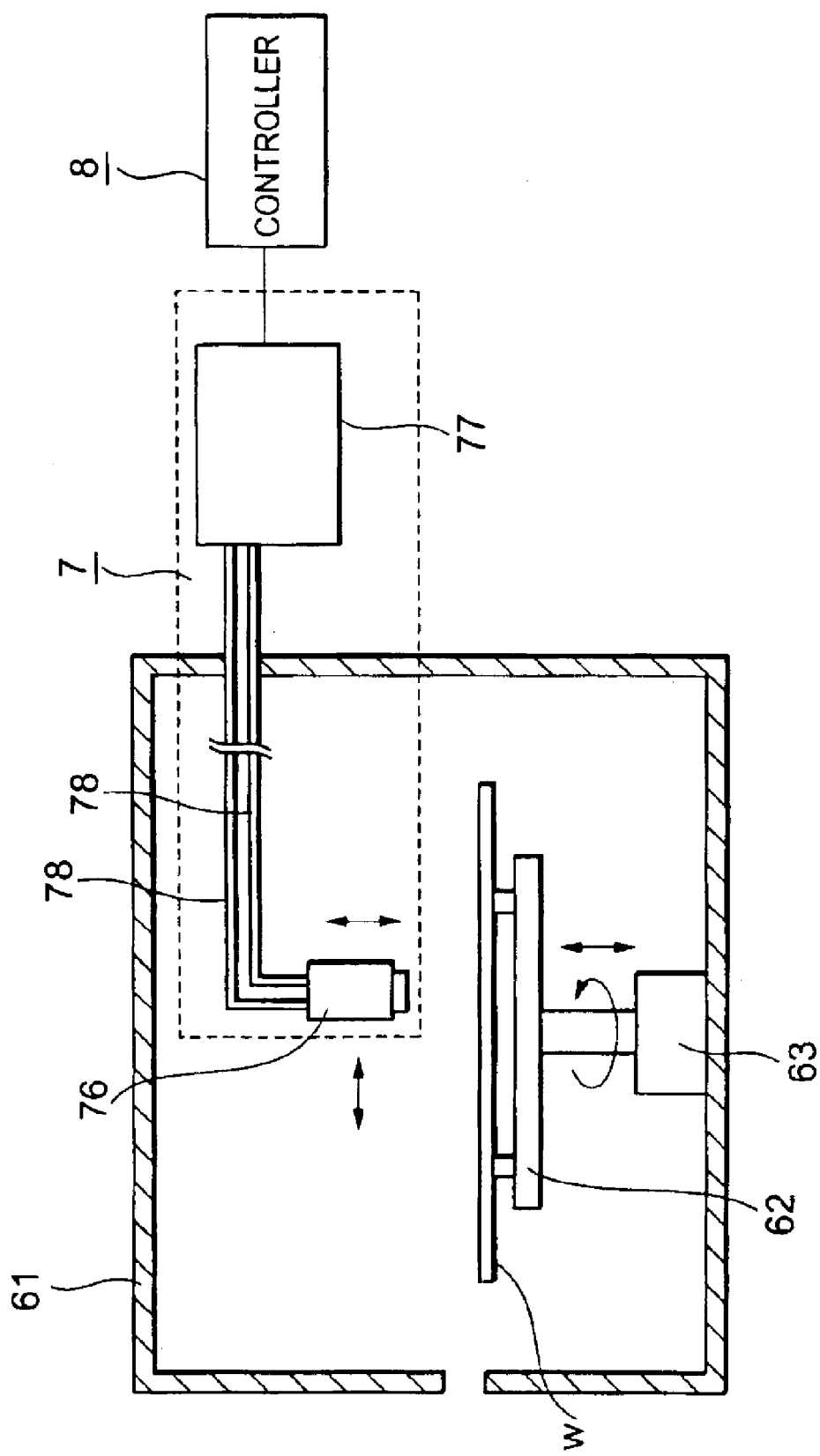
FIG. 8 is a schematic diagram showing an embodiment of an inspection apparatus involving the invention.

Subsequently, an embodiment of an inspection apparatus involving the invention will be explained with reference to FIGS. 8, 9 and 10. The inspection apparatus includes mounting table 62 disposed in a casing 61 as a placing portion of a wafer W, an optical system 7 irradiating light to the wafer W on the mounting table 62 and detects light reflected therefrom, and a control portion 8 processes a detected signal. The mounting table 62 is configured to be able to move up and down and rotatable by means of a driving mechanism 63 while wafer W being supported horizontally.

Figure 9:
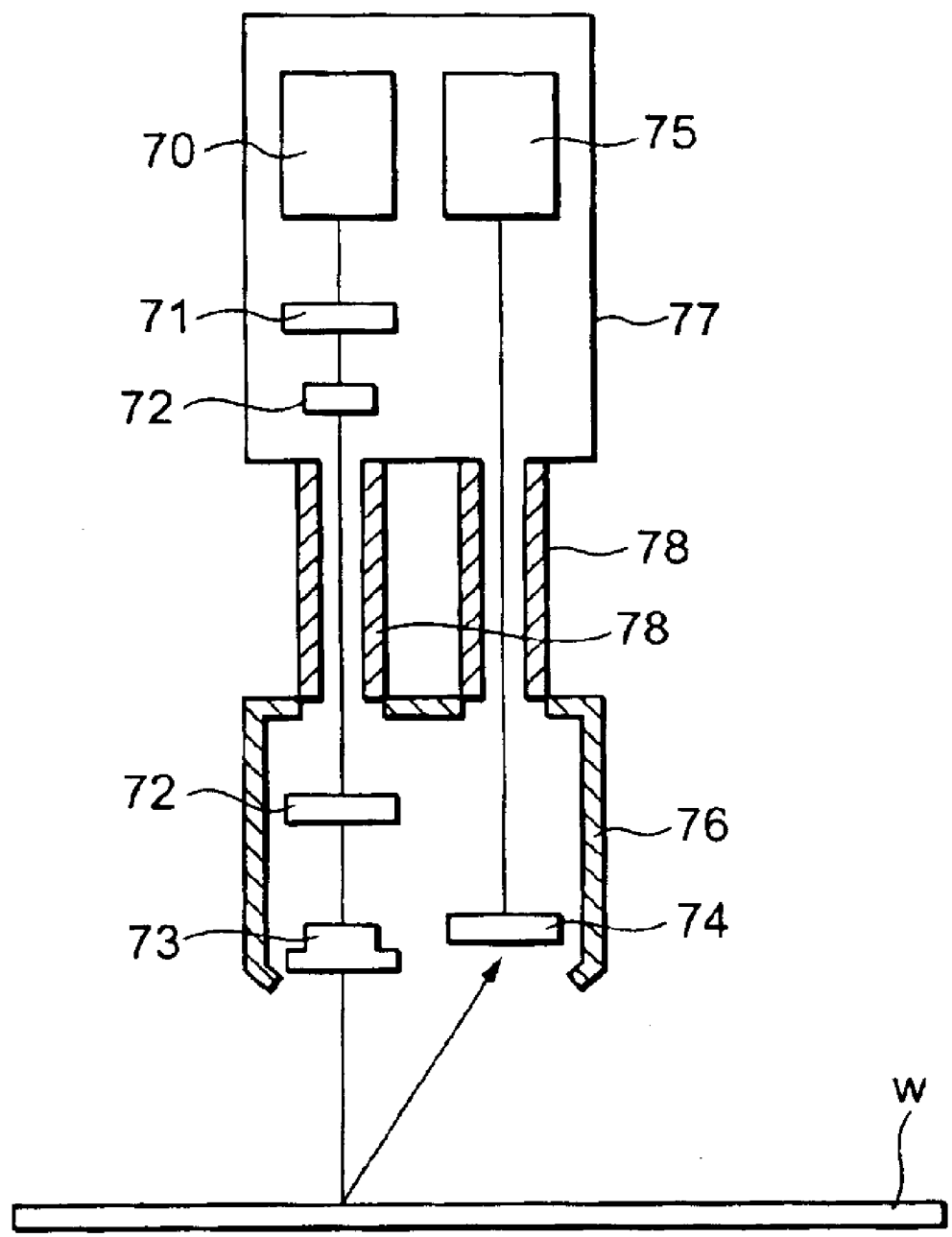
FIG. 9 is a schematic diagram showing an optical system of an embodiment of an inspection apparatus involving the invention.

The optical system 7 is constituted of, as shown in FIG. 9, a diffraction grating 71 and an optical filter 72 for monochromatizing light having a particular wavelength from light of a light source 70 such as a xenon lamp, irradiating means made of a lens 73 for focusing light and inputting to the wafer W, and detecting means made of a photo-diode 74 for detecting light reflected by the wafer W and an amplifier 75. In this case, a probe 76 movable so as to be able to irradiate on an arbitrary site on a surface of the wafer W, the optical filter 72, the lens 73 and the photo-diode 74 are disposed, in an external unit 77 disposed outside of the casing 61 in which the light source 70 and the amplifier 75 are disposed, and each of them are being connected with each other through an optical fiber 78.

Figure 10:
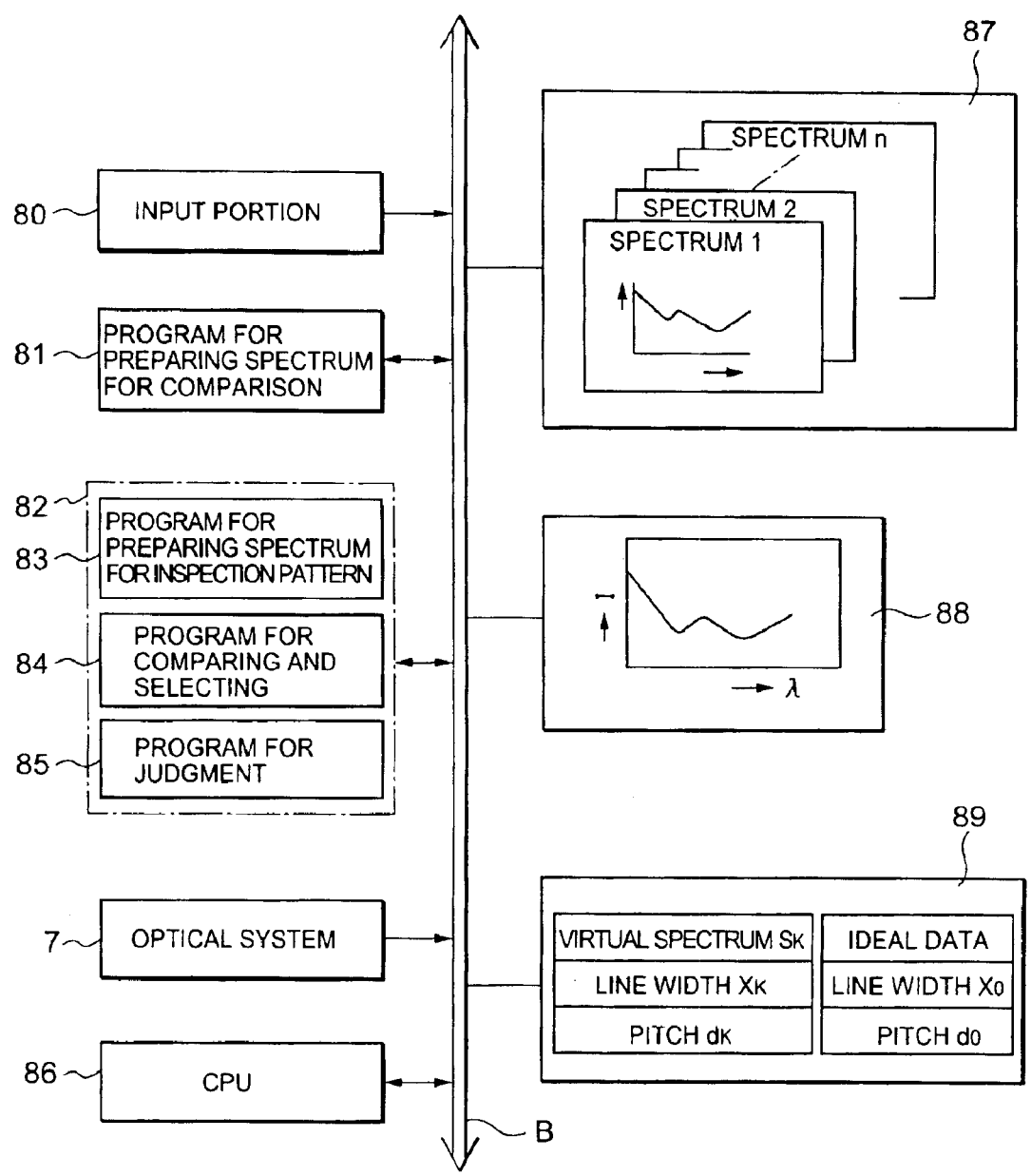
FIG. 10 is an explanatory diagram showing a controlling portion of an embodiment of an inspection apparatus involving the invention.

Furthermore, the control portion 8 is actually a computer system constituted of a CPU, a memory and a program, however, here, explanation is made as separating the elements by function as shown in FIG. 10. Numeral 80 denotes an input portion such as a keyboard and a touch panel for inputting parameters of a virtual model. Numeral 81 denotes a memory portion 81 storing a program for preparing a spectrum for comparison. Numeral 82 denotes a storing portion 82 storing a program 83 for preparing a spectrum for inspection pattern, a comparison/selection program 84 for comparing a spectrum S for inspection pattern with a group of spectra for comparison S1~Sn and selecting a inspection pattern, and a judgment program 85 judging whether the finished product is acceptable or not from estimated line width and overlay. Numeral 86 denotes a CPU and numeral 87 denotes a storing portion 87 storing a prepared group of spectra for comparison S1~Sn. Numeral 88 denotes a storing portion storing the prepared spectrum S for inspection pattern, and numeral 89 denotes a storing portion storing parameters of a selected spectrum Sk and ideal data. B denotes a bus and to the bus B the above-mentioned optical system 7 is connected.

Figure 11:
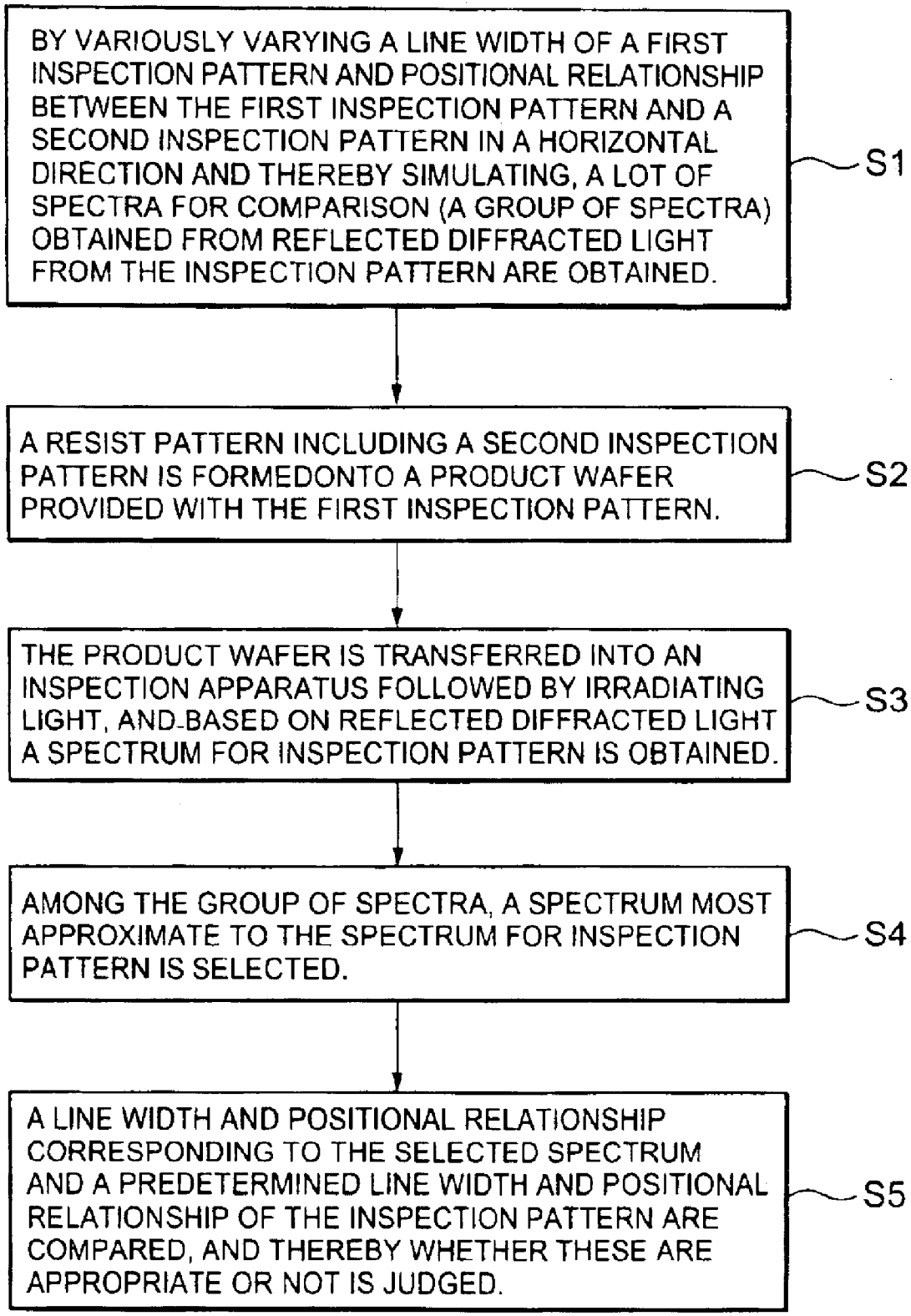
FIG. 11 is a process diagram showing a process of inspection of an inspection apparatus involving the invention.

In the next place, a process of inspection using the inspection apparatus will be explained. Firstly, as shown in step S1 in FIG. 11, a line width of the first inspection pattern 2 and a separation distance (positional relationship in a horizontal direction) between the first inspection pattern 2 and the second inspection pattern 3 which is parameter values arranged for a virtual model before the inspection is performed are inputted from an input portion 80. A spectrum for comparison S1 corresponding to the parameters is prepared according to the program 81. Then, a group of spectra for comparison S1~Sn is prepared by variously varying the parameter values and stored in the storing portion 87. The group of spectra for comparison S1~Sn is prepared in the number of, for instance, 200,000 to 500,000.

Then, as shown in step S2, the wafer W on which the first inspection pattern 2 has been formed, after a resist is coated, the inspection pattern 2 is exposed with an exposure mask having a shape corresponding to a pattern including a circuit pattern and a second inspection pattern 3 then subjected to developing process, thereby a resist pattern including the second inspection pattern 3 is formed on the surface of the wafer W. The wafer W, as shown in step S3, is placed on a rotatable mounting table 62 by means of a not shown transferring arm, and the probe 76 moves horizontally to a position corresponding to the pattern for inspection made of the first inspection pattern 2 and the second inspection pattern 3 formed on a surface of the wafer W. Then the probe 76 moves down and thereby set at a pre-determined height, for instance, 1 to 20 mm from the surface of the wafer W.

Next, light emitted from the light source 70 travels through the diffraction grating 71 and the optical filter 72 and becomes a light having a particular wavelength λ arranged in the range of, for instance, 300 to 700 nm. The light is being focused through a lens 73, then being irradiated on the wafer W from the right above thereof. Diffracted light, i.e. reflected light, is detected with the photodiode 74, and being taken into the control portion 8 through the amplifier 75 as data for preparing the spectrum for inspection pattern S, and the spectrum S for inspection pattern is prepared by means of the program 83 and stored in the memory portion 88.

Furthe, as shown in a step S4, the spectrum for inspection pattern S is compared by means of the comparison/selection program 84 with the group of spectra for comparison S1~Sn in the storing portion 87, a spectrum for comparison Sk, which is the same as or most approximate to the spectrum for inspection pattern S is selected and stored in the storing portion 89. The line width xk and the pitch dk of the spectrum for comparison Sk are estimated to be the line width x and the pitch d of the inspection pattern.

On the other hand, in the storing portion 89, a line width x0 and a pitch d0 (ideal data) of a scheduled pattern are stored, as shown in a step S5. The estimated line width xk and x0 are compared, and estimated pitch dk and d0 are compared by use of the judgment program 85, and whether the wafer W is an acceptable product or not is judged according to whether an extent of difference in the compared values is within a predetermined standard (allowable range). Here, one set of inspection patterns such as inspection patterns arranged in an X-direction is judged, subsequently inspection patterns arranged in a Y-direction are inspected according to the similar method.

According to the embodiment, based on the spectrum for inspection pattern S obtained by irradiating light, the line width of the resist pattern and the positional relationship (overlay) in a horizontal direction of the resist pattern with respect to the base film can be simultaneously inspected, accordingly, a time necessary for inspection can be shortened. In addition, footprint of the inspection apparatus can be made smaller by constituting with a single inspection apparatus. Furthermore, though an additional effect, it is confirmed that when measurement accuracy is experimentally compared with that of SEM i.e. a conventional method of inspecting the line width, the above method exhibits measurement reproduction accuracy of 0.8 nm in comparison with 2 to 3 nm according to the SEM, that indicates the measurement accuracy is improved.

Another embodiment of the invention, inspection patterns formed on a surface of the wafer W, arranged in X-direction and Y-direction may be arranged crossed as shown in FIG. 12A, or may be arranged in an L-shape as shown in FIG. 12B. In this case, when light is irradiated on the all of the inspection patterns both in the X-direction and Y-direction, combinations of both parameters are contained in one spectrum for inspection S. Accordingly, the inspection can be carried out simultaneously in X-direction and Y-direction, thus, a time necessary for inspection can be shortened.

Figure 13:
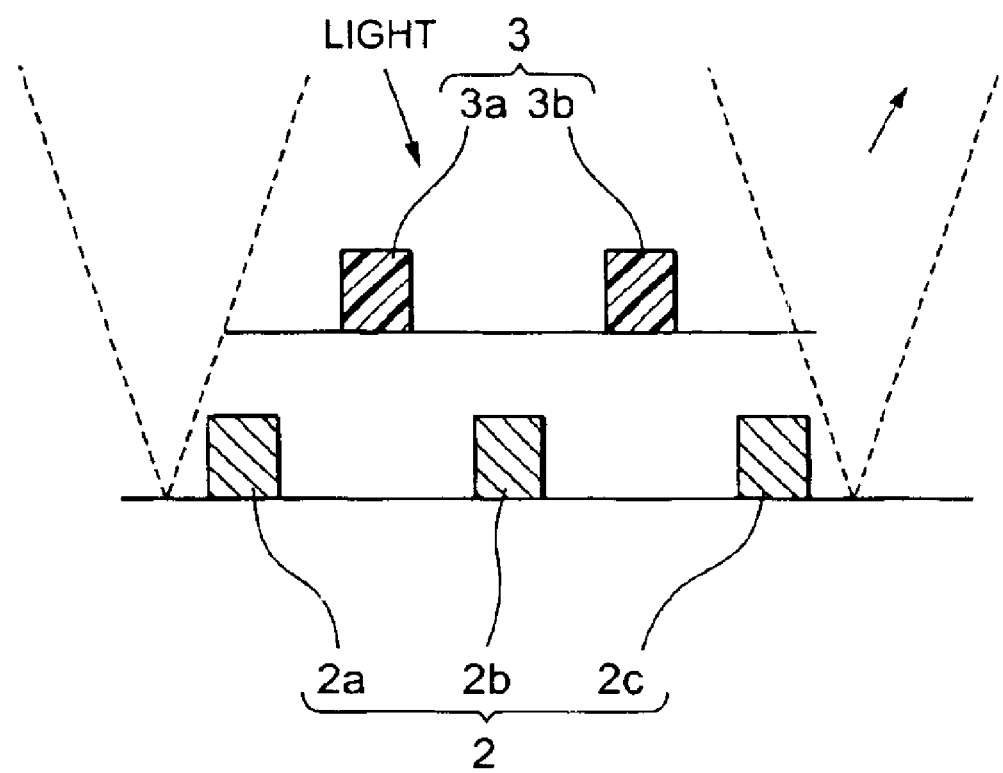
FIG. 13 is an explanatory diagram showing another embodiment of the present invention.

In addition, a method of irradiating light is not limited to the reflection incidence, as shown in FIG. 13, ellipsometric oblique incidence may also be used. In the case of such configuration, when light is irradiated on the inspection pattern, at least one result of relationship between a wavelength $\lambda$ and a phase variation of light (cos $\Delta$) containing information of both line width x and pitch d, relationship between wavelength $\lambda$ and variation of light intensity (tan $\psi$) can be obtained. Also in the ellipsometric oblique incidence, when, two sets of inspection patterns arranged in a X-direction and a Y-direction, and irradiation of one set is completed, the wafer W is rotated by 90°, followed by irradiation of the other inspection patterns. Thereby, a line width x and a pitch d of the inspection patterns in the X-direction and the Y-direction can be specified. For this reason, the same effect as that in the above case can be obtained.

Figure 14A:
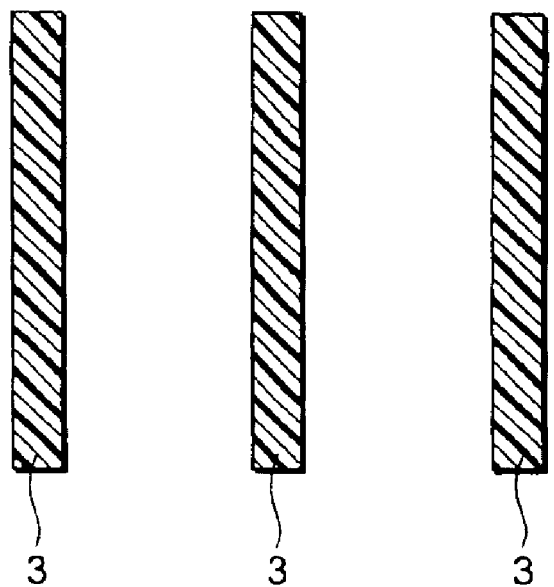
FIGS. 14A and 14B are explanatory diagrams showing another embodiment of the present invention.
Figure 14B:
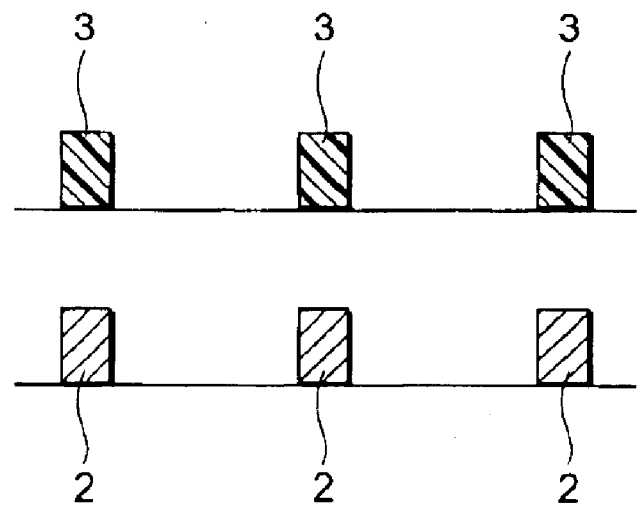

Another embodiment of the present invention is shown in FIGS. 14A and 14B. FIG. 14A is a top plan view of an inspection pattern and FIG. 14B is a side view thereof. As shown in FIG. 14A, a first inspection pattern 2 and a second inspection pattern 3 are disposed at the same positions in a plan view. That is, as shown in FIG. 14B, the first inspection pattern 2 and the second inspection pattern 3 are disposed superposed in a direction perpendicular to a surface of a substrate. Even in such inspection pattern, similarly to the above embodiment, when a spectrum for the inspection pattern shown in FIGS. 14A and 14B is compared with a spectrum for comparison, a line width and a pitch of the inspection pattern can be estimated.

Figure 15:
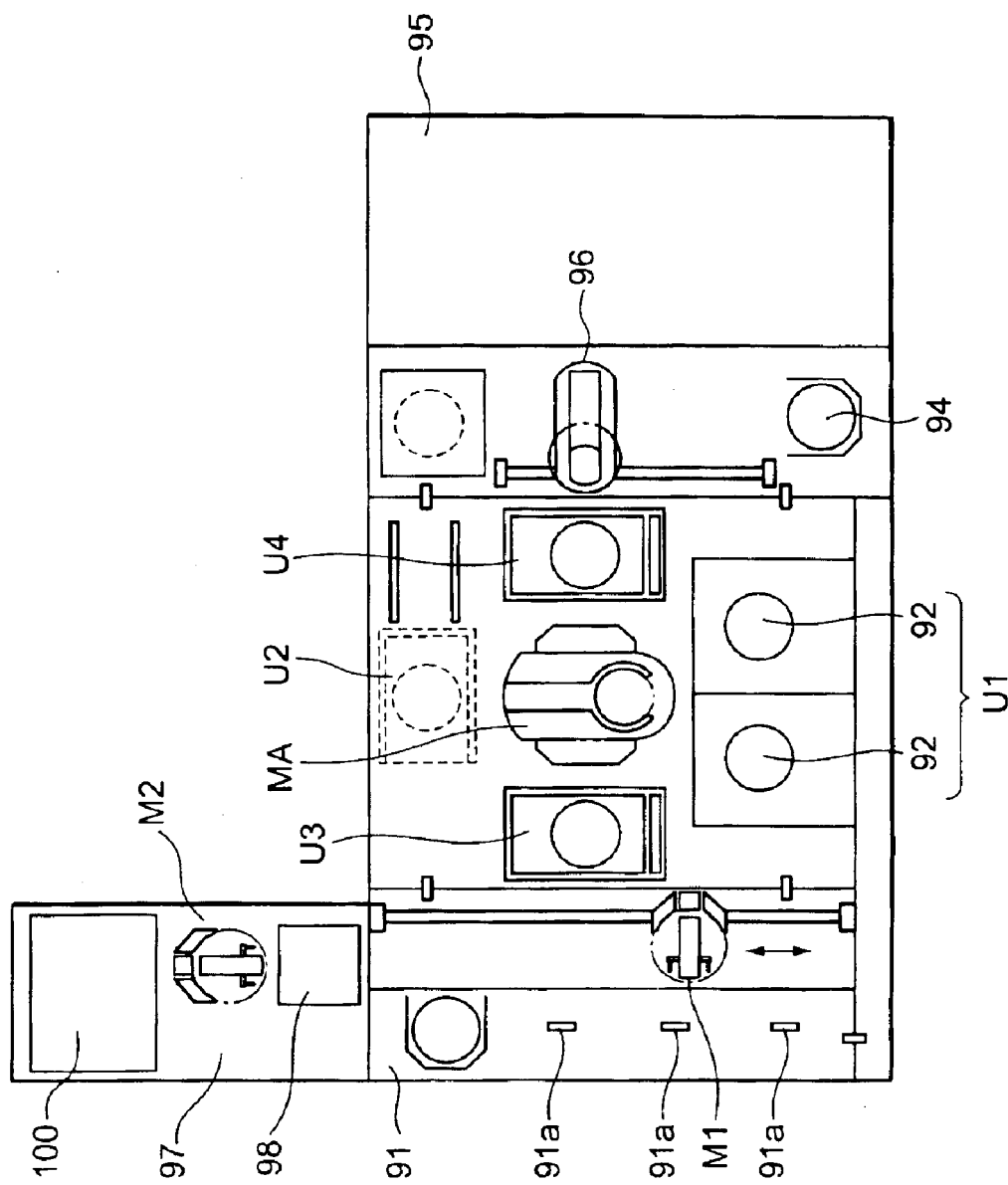
FIG. 15 is a plan view showing one example of a coating/developing apparatus in which the inspection apparatus is assembled.
Figure 16:
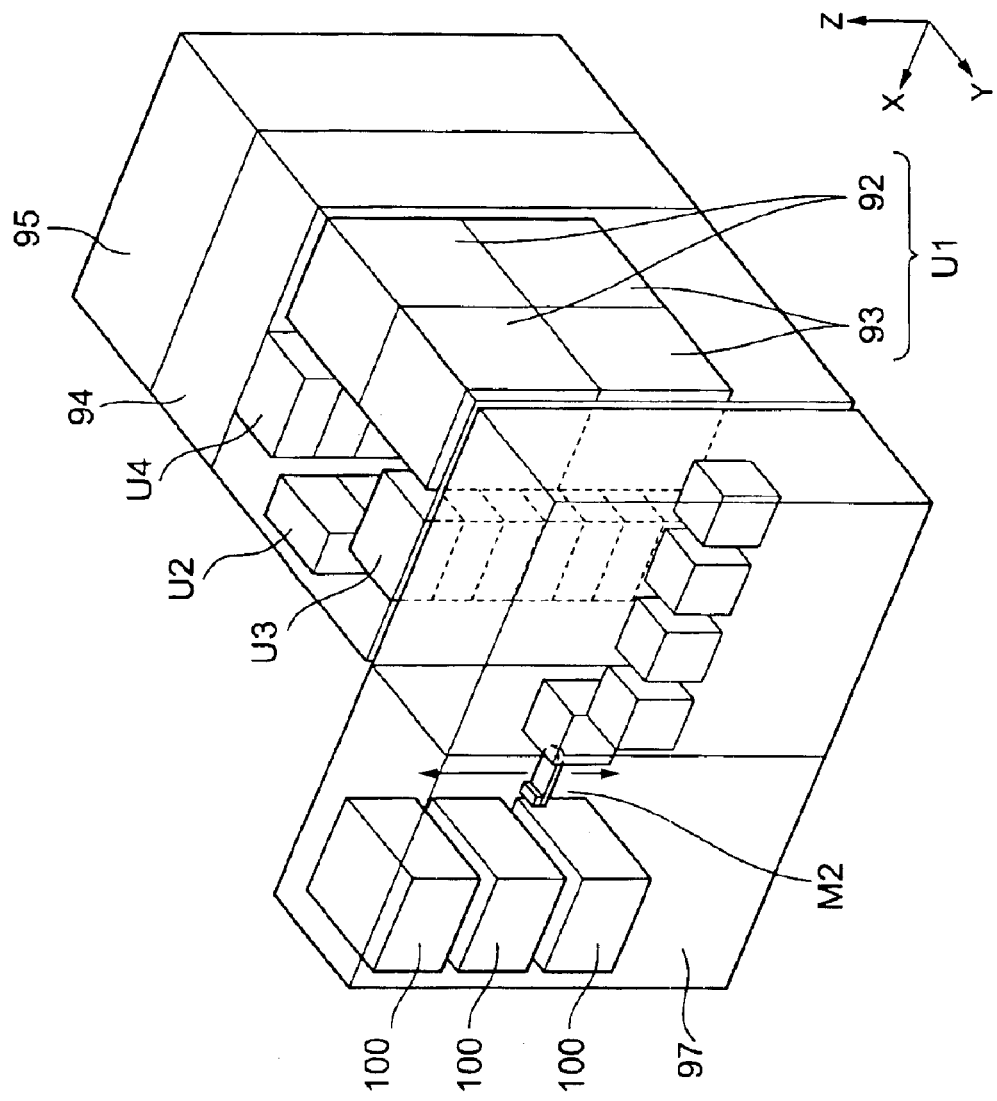
FIG. 16 is a perspective view showing one example of a coating/developing apparatus in which the inspection apparatus is assembled.
Figure 17A:
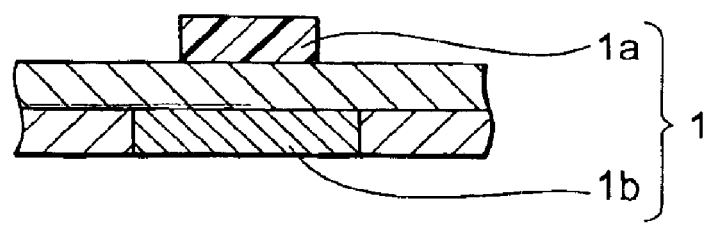
FIGS. 17A and 17B are explanatory diagrams showing an existing inspection method of an inspection apparatus.
Figure 17B:
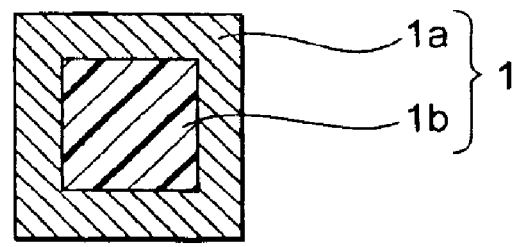

In the next place, an embodiment in which the above-mentioned inspection apparatus is built-in a coating/developing apparatus of a substrate will be explained with reference to FIGS. 15 and 16. In FIGS. 15 and 16, numeral 91 denotes a cassette station for loading and unloading a cassette C in which, for instance, 25 wafers are stored. The cassette station 91 is provided with a mounting portion 91a for placing the cassette C and a transfer arm M1 for taking out a wafer W from the cassette C and transferring the same. In a backside of the cassette station 91, when the backside is seen from, for instance, the cassette station 91, for instance on a right side, a coating/developing unit U1, and on a left side, a front side and a backside, respectively, shelf units U2, U3 and U4 in which thermal (heating/cooling system) units are stacked in multi-stage are disposed. And a transfer arm MA is disposed for delivering a wafer W between the coating/developing unit U1 and the shelf units U2, U3 and U4. In FIG. 16, the transfer arm M1, the unit U2 and the transfer arm MA are not drawn for convenience. Further, in this example, the transfer arms M1 and MA constitute transfer means for transferring a wafer W between the cassette C and each of the units U1~U4.

In the coating/developing unit U1, for instance, on an upper stand, a developing unit 92 provided with two of the developing apparatuses is disposed, and on a lower stand, a coating unit 93 provided with two of the coating apparatuses is disposed. In the shelf units U2, U3 and U4, other than the heating unit and the cooling unit i.e. thermal processing portions, a wafer delivering unit and a hydrophobic processing unit are disposed one on top of the other.

When a portion where the transfer arm MA and the coating/developing unit U1 are disposed is called as a processing block, the processing block is connected to an aligner 95 through an interface unit 94. The interface unit 94 transfers a wafer W with wafer W transfer means 96 between the processing block and the aligner 95.

Figure 7:
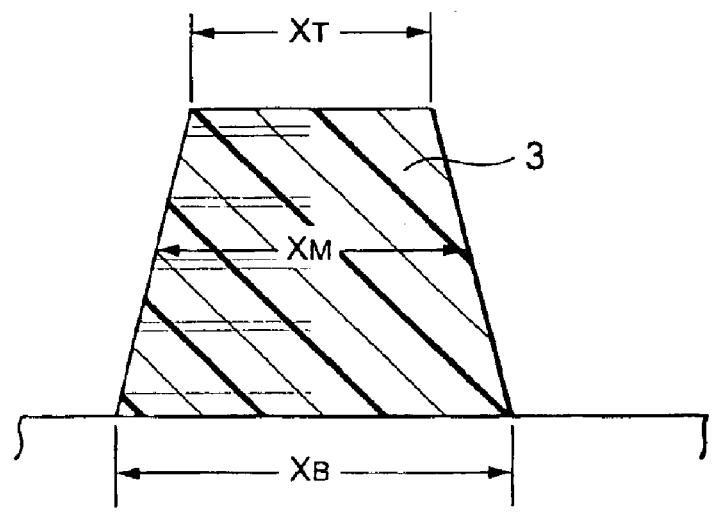
FIG. 7 is an explanatory diagram showing an inspection method of an inspection apparatus involving the present invention.

In addition, an inspection apparatus 100 such as an inspection apparatus shown in, for instance, FIG. 7 that performs the above-mentioned inspections to a wafer after being subjected to the coating and the developing process is disposed in an inspection station 97 adjacent to the cassette station 91 with a structure that three inspection apparatuses 100, for instance, are stacked up and down. An auxiliary arm M2 for transferring the wafer W to these inspection apparatuses 100 is configured rotatable and capable of moving up and down. Still furthermore, both sides are opened so that the auxiliary arm M2 and the transfer arm M1, respectively, may be able to transfer the wafer W in and out. An intermediate mounting table 98 provided with shelves capable of holding, for instance, 25 wafers is disposed inside the inspection station 97. The wafer W is transferred between the inspection station 97 and the cassette station 91 through the intermediate mounting table 98.

A flow of a wafer in the apparatus will be explained. Firstly, a wafer cassette C in which wafers W on each of which a first inspection pattern 2 is formed are housed is externally placed on a susceptor 91a, and a transfer arm M1 takes out a wafer W from inside thereof and delivers to a transfer arm MA through a delivering table disposed in one of a shelf of the heating/cooling unit U3. Subsequently, in a processing portion of a shelf of the unit U3, a hydrophobic process is carried out followed by coating of a resist solution at a coating unit 92, and thereby a resist film is formed.

The wafer W coated with the resist film is heated at the heating unit then, after being subjected to heating process, the wafer W is transferred to a cooling unit that is capable of transferring wafer W with transfer means 96 of the interface unit 94 of the unit U4. After the processing, the wafer is transferred to an aligner 95 through the interface unit 94 and the transfer means 96 and subjected to exposing process through a mask corresponding to a pattern including a circuit pattern and a second inspection pattern 3. The exposed wafer is received by the transfer means 96 and transferred through a transfer unit of the unit U4 to the wafer transfer arm MA of a processing block. When exposing, in order to suppress the accuracy of the overlay from deteriorating owing to expansion and contraction of the wafer W, temperatures inside the interface unit 94 and the aligner 95 are preferably maintained substantially the same.

Thereafter, the wafer W is heated to a predetermined temperature at the heating unit followed by cooling to a predetermined temperature at the cooling unit, subsequently transferred to the developing unit 93 to develop, and thereby the resist pattern and the second inspection pattern 3 are formed. Thereafter, the wafer to be inspected is transferred to an intermediate mounting table 98 by the transfer arm M1, placed on amounting table 62 by an auxiliary arm M2 disposed in the inspection apparatus, transferred out by means of the auxiliary arm M2 after the inspection, and returned to the inside of the cassette C through the intermediate mounting table 98 by the transfer arm M1. An acceptable wafer W is transferred to a subsequent etching process. On the other hand, the rejected wafer W, is set again on the susceptor 91a of the coating/developing apparatus after the resist on the surface is removed, then subjected to the similar process, and thereby a resist pattern is formed. The wafers W rejected according to inspection results may be discriminated and placed in a cassette for housing rejected wafers W prepared in advanced on the mounting portion 91a.

In the case of the embodiment of this kind, not only effects similar to the above-mentioned effects can be obtained, but also, owing to the integration of the inspection process into the photo-resist process of the wafer W, a time consumed for transferring the wafer W between the coating/developing apparatus and the inspection apparatus and selection of the rejected wafers can be shortened. Accordingly, the inspection time can be further shortened, resulting in prevention of a decreased throughput.

Furthermore, in the present invention, the inspection is not limited to the line width and the overlay, but the present invention may include a film thickness of the second inspection pattern, that is, the resist pattern as an inspection item. In other words, in addition to the line width and the pitch, by variously varying a parameter value of the film thickness of the second inspection pattern, a group of spectra for comparison S1~Sn corresponding to combinations thereof is prepared. These spectra are compared with a spectrum for inspection pattern S and being selected, as in the above case, and thereby a line width, a pitch and a resist film thickness of the inspection pattern are specified. In this case, the inspections of the line width, the overlay and the resist film thickness can be performed with a single inspection apparatus and in a single process accordingly, the shortening of the time necessary for inspection and the reduction of the footprint of the inspection apparatus can be achieved. Furthermore, the present invention can be applied also to inspect, as a substrate to be processed, other than a semiconductor wafer, such as a LCD substrate and a reticle substrate for photo-mask.

INDUSTRIAL APPLICABILITY

As mentioned above, according to the present invention, with a single substrate inspection apparatus, in a single process, a line width of a resist pattern and positional relationship (overlay) with a base film in a horizontal direction can be inspected. Accordingly, a time necessary for inspecting a substrate can be shortened and a footprint of the substrate inspection apparatus can be made smaller.

What is claimed is:

1. A substrate inspection apparatus for inspecting a substrate with a resist being coated on a surface thereof and the coated resist being performed with exposing and developing process, comprising:
    a substrate mounting portion for mounting the substrate;
    light irradiating means for irradiating a light having a predetermined wavelength from a surface side of the substrate to a region including a first inspection pattern formed on a base film and a second inspection pattern formed on a resist;
    a light detection portion for detecting the light irradiated from the light irradiating means and reflected at the surface of the substrate;
    means for preparing a spectrum for an inspection pattern from a diffracted light based on an output detected by the light detection portion;
    means for preparing, by variously varying the respective line widths of the first inspection pattern and the second inspection pattern and a mutual positional relationship in a horizontal direction of the first inspection pattern and the second inspection pattern, the group of spectra for comparison respectively corresponding to combinations of the line width of the second inspection pattern and the mutual positional relationship; and
    comparison and selection means for comparing the group of spectra for comparison and the spectrum for inspection pattern and selecting one most approximate to the spectrum for inspection among the group of spectra for comparison;
    wherein from the selected spectrum for comparison, a line width of the second inspection pattern which is a resist pattern formed on the substrate, and the positional relationship in a horizontal direction on the substrate are estimated.

2. The substrate inspection apparatus, as set forth in claim 1, further comprising:
    judging means for judging whether a line width of the resist pattern and a mutual positional relationship in a horizontal direction of the resist pattern and the base film are appropriate or not based on a line width and the positional relationship of the second inspection pattern corresponding to a selected spectrum for comparison and an allowable line width and an allowable positional relationship of the second inspection pattern.

3. The substrate inspection apparatus, as set forth in claim 1 or 2,
    wherein each of the first inspection pattern and the second inspection pattern is formed in quadrangle and arranged alternately on a straight line in a top plan view.

4. The substrate inspection apparatus, as set forth in claim 1 or 2,
    wherein a set in which the first inspection pattern and the second inspection pattern are arranged on a straight line in the X-direction and a set in which a first inspection pattern and a second inspection pattern are arranged on a straight line in a Y-direction, and for each of the sets a spectrum for inspection pattern is formed and a most approximate spectrum for comparison is selected, and whether each of a mutual positional relationship of the resist pattern and the base film in the X direction and a mutual positional relationship thereof in the Y direction is appropriate or not is judged based on the spectrum for comparison.

5. The substrate inspection apparatus, as set forth in claim 1 or 2,
    wherein the first inspection pattern and the second inspection pattern are arranged equidistantly apart.

6. The substrate inspection apparatus, as set forth in claim 1 or 2,
    wherein the first inspection pattern and the second inspection pattern are formed outside of an effective region of a substrate.

7. The substrate inspection apparatus, as set forth in claim 1 or 2,
    wherein the first inspection line and the second inspection line are formed in a scribe line cut for each chip.

8. The substrate inspection apparatus as set forth in claim 1 or 2,
    wherein means for preparing the group of spectra for comparison has a simulation means for preparing the spectrum for comparison owing to simulation based on a set of the line width and the positional relationship.

9. The substrate inspection apparatus as set forth in claim 1 or 2, wherein each of the first inspection pattern and the second inspection pattern is formed in quadrangle and arranged on the same position on a straight line in a top plan view.

10. A coating/developing apparatus, comprising:

a substrate inspection apparatus as set forth in any claim 1 or 2, a mounting portion for mounting a substrate cassette housing a plurality of substrates;

a coating unit for coating a resist on the substrate;

a developing unit for developing an exposed substrate;

a thermal unit for heating and cooling the substrate before or after the coating the resist on the substrate, or, before or after developing the substrate; and transferring means for transferring a substrate between the mounting portion, the coating unit, the developing unit and the thermal unit.

11. A substrate inspection method for inspecting a substrate with a resist being coated on a surface thereof and the coated resist being performed with exposing and developing process, comprising:

transferring a substrate into a substrate mounting portion for mounting the substrate;

irradiating a light having a predetermined wavelength from a surface side of the substrate to a region including a first inspection pattern formed on a base film and a second inspection pattern formed on a resist and detecting the light irradiated from the light irradiating means and reflected at the surface of the substrate with a light detection portion;

preparing a spectrum for an inspection pattern from a diffracted light based on an output detected by the light detection portion;

selecting one most approximate to the spectrum for inspection by comparing the spectrum for inspection pattern with a group of spectra which is prepared in advance by variously varying the respective line widths of the first inspection pattern and the second inspection pattern and mutual positional relationships in a horizontal direction of the first inspection pattern and the second inspection pattern, the group of spectra for comparison respectively corresponding to combinations of the line width of the second inspection pattern and the mutual positional relationship; and estimating a line width of the second inspection pattern which is a resist pattern formed on the substrate, and the positional relationship in a horizontal direction on the substrate.

12. The substrate inspection method according to claim 11, further comprising:

judging means for judging whether a line width of the resist pattern and a mutual positional relationship in a horizontal direction of the resist pattern and the base film are appropriate or not based on a line width and the positional relationship of the second inspection pattern corresponding to a selected spectrum for comparison and an allowable line width and an allowable positional relationship of the second inspection pattern.

* * * * *